US009937137B2

(12) United States Patent
Liu et al.

(10) Patent No.: US 9,937,137 B2
(45) Date of Patent: Apr. 10, 2018

(54) MAGNESIUM COMPOSITIONS AND USES THEREOF FOR CANCERS

(71) Applicant: Neurocentria, Inc., Hayward, CA (US)

(72) Inventors: Guosong Liu, Sunnyvale, CA (US); Fei Mao, Fremont, CA (US)

(73) Assignee: Neurocentria, Inc., Walnut Creek, CA (US)

( * ) Notice: Subject to any disclaimer, the term of this patent is extended or adjusted under 35 U.S.C. 154(b) by 0 days.

(21) Appl. No.: 14/764,944

(22) PCT Filed: Mar. 14, 2014

(86) PCT No.: PCT/US2014/028542
§ 371 (c)(1),
(2) Date: Jul. 30, 2015

(87) PCT Pub. No.: WO2014/144227
PCT Pub. Date: Sep. 18, 2014

(65) Prior Publication Data
US 2015/0366828 A1 Dec. 24, 2015

Related U.S. Application Data

(60) Provisional application No. 61/800,202, filed on Mar. 15, 2013.

(51) Int. Cl.
A61K 31/191 (2006.01)
A61K 31/195 (2006.01)
A61K 33/06 (2006.01)
A61K 45/06 (2006.01)

(52) U.S. Cl.
CPC .......... A61K 31/191 (2013.01); A61K 31/195 (2013.01); A61K 33/06 (2013.01); A61K 45/06 (2013.01)

(58) Field of Classification Search
CPC ...... A61K 45/06; A61K 31/195; A61K 33/06; A61K 2300/00
USPC .......................................... 424/451; 514/557
See application file for complete search history.

(56) References Cited

U.S. PATENT DOCUMENTS

| 2004/0242679 | A1 | 12/2004 | Jariwalla |
| 2006/0089335 | A1 | 4/2006 | Liu et al. |
| 2008/0248100 | A1 | 3/2008 | Liu et al. |
| 2008/0249169 | A1 | 3/2008 | Liu et al. |
| 2010/0209388 | A1 | 1/2010 | Mazzio et al. |
| 2011/0020443 | A1* | 1/2011 | Liu .................. A61K 31/191 424/464 |

FOREIGN PATENT DOCUMENTS

| WO | WO 97/22596 A1 | 6/1997 |
| WO | WO 97/30035 A1 | 8/1997 |
| WO | WO 97/32856 A1 | 9/1997 |
| WO | WO 98/13354 A1 | 4/1998 |
| WO | WO 99/02166 A1 | 1/1999 |
| WO | WO 00/40529 A1 | 7/2000 |
| WO | WO 00/41669 A1 | 7/2000 |
| WO | WO 00/47212 A1 | 8/2000 |
| WO | WO 01/92224 A1 | 12/2001 |
| WO | WO 01/94341 A1 | 12/2001 |
| WO | WO 02/04434 A1 | 1/2002 |
| WO | WO 02/08213 A1 | 1/2002 |

OTHER PUBLICATIONS

Hodgkinson et al; title: Magnesium depletion in patients receiving cisplatin-based chemotherapy. Clin Oncol (R Coll Radiol). 2006;18(9): 710-718.*
Hunter et al; Title: Evaluation of intervention to prevent hypomagnesemia in cervical cancer patients receiving combination cisplatin and radiation treatment; Support Care Cancer. Sep. 2009;17(9):1195-201. Epub Jan. 27, 2009.*
Artherholt, et al. Psychosocial care in cancer. Curr Psychiatry Rep. Feb. 2012;14(1):23-9. doi: 10.1007/s11920-011-0246-7.
Cryan, et al. Assessing antidepressant activity in rodents: recent developments and future needs. Trends Pharmacol Sci. May 2002;23(5):238-45.
Donaldson. Nutrition and cancer: a review of the evidence for an anti-cancer diet. Nutr J. Oct. 20, 2004;3:19.
International preliminary report on patentability dated Sep. 24, 2015 for PCT/US2014/028542.
International search report and written opinion dated Jul. 28, 2014 for PCT/US2014/028542.
Kozielec, et al. Assessment of magnesium levels in children with attention deficit hyperactivity disorder (ADHD). Magnes Res. Jun. 1997;10(2):143-8.
Lombardo, et al. Discovery of N-(2-chloro-6-methyl- phenyl)-2-(6-(4-(2-hydroxyethyl)- piperazin-1-yl)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.
Mousain-Bosc, et al. Improvement of neurobehavioral disorders in children supplemented with magnesium-vitamin B6. I. Attention deficit hyperactivity disorders. Magnes Res. Mar. 2006;19(1):46-52.
Porsolt, et al. Depression: a new animal model sensitive to antidepressant treatments. Nature. Apr. 21, 1977;266(5604):730-2.
Slutsky, et al. Enhancement of synaptic plasticity through chronically reduced Ca2+ flux during uncorrelated activity. Neuron. Dec. 2, 2004;44(5):835-49.
Stern, et al. Overview of monoclonal antibodies in cancer therapy: present and promise. Crit Rev Oncol Hematol. Apr. 2005;54(1):11-29.
Thomas, et al. Evaluation of threonic acid toxicity in small animals. Food Chem. 1985; 17:79-83.

(Continued)

Primary Examiner — Yanzhi Zhang
(74) Attorney, Agent, or Firm — Wilson Sonsini Goodrich & Rosati

(57) ABSTRACT

Compositions and methods that are useful for treating a subject suffering from one or more cancers are provided herein. Such compositions and methods can contain an effective amount of magnesium threonate to be used to support or improve the mental state of a subject. The composition and methods comprising magnesium threonate can also be used to support a cancer treatment.

15 Claims, No Drawings

(56) References Cited

OTHER PUBLICATIONS

Tuma, et al. Altered mental status in patients with cancer. Arch Neurol. Dec. 2000;57(12):1727-31.
Verlangieri, et al. Comparison of the anti-scorbutic activity of L-ascorbic acid and Ester C in the non-ascorbate synthesizing Osteogenic Disorder Shionogi (ODS) rat. Life Sci. 1991;48(23):2275-81.
Weinberger, et al. Women at a dangerous intersection: diagnosis and treatment of depression and related disorders in patients with breast cancer. Psychiatr Clin North Am. Jun. 2010;33(2):409-22. doi: 10.1016/j.psc.2010.01.005.

\* cited by examiner

MAGNESIUM COMPOSITIONS AND USES THEREOF FOR CANCERS

CROSS REFERENCE

This application claims priority to U.S. Provisional Patent Application No. 61/800,202, filed on Mar. 15, 2013, which is entirely incorporated herein by reference.

BACKGROUND OF THE INVENTION

It has been reported that a person would exhibit an altered or declined mental state when the person is suffering from cancer (Tuma et al., *Altered Mental Status in Patients With Cancer*, Arch Neurol. 2000;57(12):1727-1731). Depression, anxiety, delirium, impaired cognitive functions, and other mental health declines are found to be closely associated with cancer. For example, delirium, one condition that is associated with a decline of mental state as measured by the mental state examination (MSE), is reported to be present in about 14% to 40% of patients hospitalized with cancer, and appears to be associated with an increased mortality rate. About 25% of cancer patients meet the criteria for an anxiety disorder, with about 3% suffering post-traumatic stress disorder (Fletcher et al., Clinical Oncological Society of Australia's Annual Scientific Meeting, 2010). A cancer diagnosis is often accompanied with swift and aggressive anti-cancer treatment, and a person may be overwhelmed, worried, fearful, and anxious under the treatment. Decline of the mental state can prolong hospital stay, may make the patient less engaged in anti-cancer treatments, and can cause morbidity.

Decline of mental state in cancer patients has poor prognosis. However, early recognition of declined mental state and proper treatment to restore the mental status can be beneficial to the recovery of the cancer patients. In some cases, hospital time can be shortened, and patients may recover remarkably. Depression, for example, is strongly associated with reduced cancer survival (Cancer Council Australia. *Depression Associated With Reduced Cancer Survival*. Medical News Today. MediLexicon, Intl., 10 Nov. 2010). Studies have described that those who were not depressed, but actually felt hopeful, were more likely to recover than those who were depressed. Improving the mental state of the patients can encourage the patients to take an active role in their treatment decisions and be more engaged in their recovery. In current anti-cancer treatments, medical doctors focus heavily and primarily on the anti-cancer medical treatment of a cancer patient, and treating the mental state decline is often neglected or under-addressed. Currently, it appears that there has not been an effective treatment course targeting improvement of the mental state of cancer patients to support them through the anti-cancer treatment. Effective and reliable treatment methods to improve the mental state of persons suffering from cancer or to support their anti-cancer treatments appear to be in clinical mandate as indicated in Weinberger et al, *Women at a Dangerous Intersection: Diagnosis and Treatment of Depression and Related Disorders in Patients with Breast Cancer*. Psychiatric Clinics of North America 33.2 (2010): 409-22, and Artherholt et al., *Psychosocial Care in Cancer Patients*. Curr. Psychiatry Rep (2012): 14:23-29.

SUMMARY OF THE INVENTION

In view of the foregoing, there is a considerable need for compositions, uses thereof, and/or associated technology to improve the mental state of a subject that is suffering from cancer or is under a cancer therapeutic treatment. Aspects of the subject invention satisfy these needs and provide related advantages as well.

The subject application provides compositions and methods for treating a subject that is suffering from cancer. The compositions and methods can include magnesium threonate. Aspects of the present invention address the need in supporting and improving the mental state of subjects that is suffering from cancer or under cancer treatments.

The subject compositions can be administered orally or through other routes such as intravenous administration. Compositions for oral administration can include pills, tablets, capsules, and the like.

In one aspect, the current invention provides methods of treating a subject suffering from one or more types of cancer. The method comprises identifying the subject that is suffering from said one or more types of cancer; and administering to the subject a pharmaceutical composition comprising an effective amount of magnesium threonate. In some embodiments, the method can further comprise a step of treating the subject with a cancer therapeutic. In some embodiments, the pharmaceutical composition that is used in the methods described herein can further comprise one or more anti-cancer agents.

In some embodiments, the subject suffering from the one or more types of cancer in need of the compositions described herein can also suffer from depression, anxiety, dementia, insomnia, cognitive impairment, memory function decline, learning capacity decline, migraine, mood swing, hypertension, attention deficit hyperactivity disorder, Alzheimer's disease or Parkinson's disease. In some embodiments, said administering of the pharmaceutical composition in the method described herein is effective in improving mental state of said subject.

In yet another aspect, the subject in need of the composition disclosed herein can be suffering from the one or more types of cancer that is selected from the group consisting of: breast cancer, lung cancer, prostate cancer, gastric cancer, head & neck cancer, melanoma, bladder cancer, neuroendocrine cancer, squamous carcinoma, cervical cancer, vulvar cancer, thyroid cancer, pancreatic cancer, renal cancer, esophageal cancer, rectal cancer, penile cancer, lymphoma, multiple myloma, Merkel cell tumors, ovarian cancer and colorectal cancer.

The methods disclosed herein can involve administration of the pharmaceutical composition orally. In some embodiments, the pharmaceutical composition comprises 10 mg to 1.5 g elemental magnesium.

In some embodiments, the pharmaceutical composition described herein can be effective in improving one or more conditions selected from depression, anxiety, dementia, insomnia, cognitive impairment, memory function decline, learning capacity decline, migraine, mood swing, hypertension, attention deficit hyperactivity disorder, Alzheimer's disease or Parkinson's disease.

The methods as described herein can involve administering the pharmaceutical composition for at least about 1 month. In some embodiments, the pharmaceutical composition can be administered for at least about 1 week.

In some embodiments, the effective amount of magnesium threonate as disclosed in the methods can be an amount capable of achieving a physiological concentration of magnesium at 0.75 mM or above in serum, plasma, or cerebrospinal fluid. In some embodiments, said effective amount can be an amount capable of increasing a physiological concentration of magnesium by at least 10% as compared to an initial level of magnesium prior to administration of it to said subject.

In some cases, the pharmaceutical composition as described in the methods disclosed herein can be contained in a foodstuff.

The another aspect of the current invention also provides a method of supporting cancer treatment, comprising administering to a subject in need thereof one or more anticancer agents in conjunction with an amount of magnesium threonate effective in improving mental state of the subject.

In one aspect, the current invention provides a composition formulated in a solid or liquid dosage form, comprising (a) one or more anti-cancer agents; and (b) magnesium threonate. In some embodiments, the compositions described herein can be formulated in a unit dosage form.

The composition as disclosed herein can be formulated for oral consumption, intravenous injection, inhalation, nasal insufflation, intraarterial injection, intramuscular injection, topical administration, subcutaneous administration, mucosal administration, endotracheal administration, pharyngeal administration, rectal administration, sublingual administration or vaginal administration.

In some embodiments, the magnesium threonate can be present in an amount effective in improving mental state of a subject administered.

In some cases, the composition as described herein can be a pharmaceutical composition comprising a pharmaceutically active agent and an excipient wherein the excipient is magnesium threonate. In some embodiments, the composition can be a dietary supplement.

In another aspect, the composition can be formulated in a slow-release form. The composition as described herein can be formulated in a solid or liquid dosage form that can be a tablet, a capsule, a pill, an emulsion, a gel, a plurality of beads encapsulated in a capsule, a powder, a suspension, a liquid, a semi-liquid, a semi-solid, a syrup, a slurry or a chewable form.

In some embodiments, the component (a) and component (b) in the composition described herein can be separately packaged in said dosage form. In some embodiments, the component (a) and component (b) can be mixed in said dosage form.

In yet another embodiment, the one or more anti-cancer agents present in the composition disclosed herein can be present in an amount effective in treating a symptom associated with a cancer.

In still yet another embodiment, the composition disclosed herein can comprise 10 mg to 1.5 g elemental magnesium.

In some aspects, the composition disclosed in the current invention can be capable of achieving a physiological concentration of magnesium at 0.75 mM or above in serum, plasma, or cerebrospinal fluid. In another aspect, the composition can be capable of increasing a physiological concentration of magnesium by at least 10% as compared to an initial level of magnesium prior to administration of it to a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

It will be understood that a word appearing herein in the singular encompasses its plural counterpart, and a word appearing herein in the plural encompasses its singular counterpart, unless implicitly or explicitly understood or stated otherwise. Further, it will be understood that for any given component described herein, any of the possible candidates or alternatives listed for that component, can generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein is approximate, and that any numerical range includes the minimum number and the maximum number defining the range, whether the word "inclusive" or the like is employed or not, unless implicitly or explicitly understood or stated otherwise. Generally, the term "approximately" or "about" or the symbol ".about." in reference to a figure or number or amount includes numbers that fall within a range of .+−.5% of same, unless implicitly or explicitly understood or stated otherwise. Yet further, it will be understood that any heading employed is by way of convenience, not by way of limitation. Additionally, it will be understood that any permissive, open, or open-ended language encompasses any relatively permissive to restrictive language, less open to closed language, or less open-ended to closed-ended language, respectively, unless implicitly or explicitly understood or stated otherwise. Merely by way of example, the word "comprising" can encompass "comprising"-, "consisting essentially of"-, and/or "consisting of"-type language.

Generally, the term "mental state" or "state of mind" can refer to an indication of a person's mental health, emotional state, or cognitive functions of a subject. The mental state can be determined by a Mental State Examination (MSE) that is known in the art. The MSE is a structured way of observing and describing a subject's current mental state, under the domains of appearance, attitude, behavior, mood and affect, speech, thought process, thought content, perception, cognition, insight and judgment (Trzepacz, P T; Baker R W (1993), *The Psychiatric Mental Status Examination*. Oxford, U.K.: Oxford University Press. p. 202). A mental state can also refer to a kind of hypothetical state or process that corresponds to thinking and feeling, consisting of a conglomerate of mental representations and propositional attitudes. A decline in mental state can result in various psychological conditions that are known in the art, for example, depression, mood swing, anxiety disorder, delirium, dementia, insomnia, cognitive impairment, memory function decline, learning capacity decline, migraine, delusion, hallucination, disseminated systemic metastases, confusion, agitation, disorientation, reduced consciousness, perceptual disturbance, change in psychomotor activity, lateralizing sign, seizure, and the like. A mental state of a subject can further refer to the cognitive function of a subject. Generally, the term "cognition" can refer to a process of obtaining, organizing, understanding, processing, and/or using information or knowledge. Generally, enhancing cognitive function refers to enhancing any aspect of such a process, such as learning, the performance of mental operations, the storage, retrieval, and/or use of information and/or thoughts, memory, and/or preventing a decline of a subjects cognitive state, for example. Various standardized tests can be used to evaluate cognition, cognitive function, and/or cognitive state and can be used to identify a subject who might be conducive to, benefit from, and/or need, maintenance and/or enhancement of same and/or to monitor an effect of treatment relating to same. Examples of suitable tests include the Mini-Mental Status Exam (Folstein, 1975), components of the PROSPER neuropsychological test battery (Houx, 2002), and/or the like. Family history, age, and/or other factors can also be used to identify a subject who might be conducive to, benefit from, and/or need, maintenance and/or enhancement of cognition, cognitive function, and/or cognitive state.

Generally, the term "concurrent administration", "co-administration", or "administration in conjunction with" in reference to two or more subjects of administration for administration to a subject body, such as components, agents, substances, materials, compositions, and/or the like, refers to administration performed using dose(s) and time interval(s) such that the subjects of administration are present together within the subject body, or at a site of action in the subject body, over a time interval in less than de minimus quantities. The time interval can be any suitable time interval, such as an appropriate interval of minutes, hours, days, or weeks, for example. The subjects of administration can be administered together, such as parts of a single composition, for example, or otherwise. The subjects of administration can be administered substantially simultaneously (such as within less than or equal to about 5 minutes, about 3 minutes, or about 1 minute, of one another, for example) or within a short time of one another (such as within less than or equal to about 1 hour, 30 minutes, or 10 minutes, or within more than about 5 minutes up to about 1 hour, of one another, for example). The subjects of administration so administered can be considered to have been administered at substantially the same time. One of ordinary skill in the art will be able to determine appropriate dose(s) and time interval(s) for administration of subjects of administration to a subject body so that same will be present at more than de minimus levels within the subject body and/or at effective concentrations within the subject body.

When the subjects of administration are concurrently administered to a subject body, any such subject of administration can be in an effective amount that is less than an effective amount that might be used were it administered alone. The term "effective amount," which is further described herein, encompasses both this lesser effective amount and the usual effective amount, and indeed, any amount that is effective to elicit a particular condition, effect, and/or response. As such, a dose of any such subject of concurrent administration can be less than that which might be used were it administered alone. One or more effect(s) of any such subject(s) of administration can be additive or synergistic. Any such subject(s) of administration can be administered more than one time.

Generally, the term "effective amount" in reference to an active agent refers to the amount of the active agent sufficient to elicit a particular biological condition, effect, and/or response. The absolute amount of a particular agent that is effective in this manner can vary depending on various factors, such as the desired biological endpoint, the agent itself, the subject or targeted part thereof, and/or the like, for example. An effective amount of an active agent can be administered in a single dose or in multiple doses. Examples of a biological condition, effect or response that can result from an effective amount of an active agent include a maintaining and/or improving of a subjects performance of a task involving or associated with mental state or cognitive function, a maintaining and/or improving of a subject's, a maintaining and/or improving (slowing, for example) of a rate of decline in mental state or cognitive function, and/or the like, for example. A component can be described herein as having at least an effective amount, or at least an amount effective, such as that associated with a particular goal or purpose, such as any described herein.

Generally, the term "elemental magnesium" as used in connection with a magnesium-counter ion (e.g., threonate) compound described herein, refers to a total amount of magnesium that is present as free ion and magnesium that is bound with one or more counter ions (e.g., threonate). In general, such a term is not used to refer to magnesium that can be associated with an agent other than a magnesium threonate compound that can be a component of a magnesium threonate composition (e.g., a pharmaceutical composition, a dietary supplement composition, a foodstuff supplemented with a magnesium threonate). A small amount of magnesium can be naturally present in or otherwise associated with such an agent. For example, a fruit juice extract or flavoring agent can comprise an amount of magnesium from that naturally present in the fruit from which it was derived. Generally, the term "elemental magnesium" as used in connection with a magnesium threonate compound would not encompass such agent-associated magnesium.

In some aspects of the invention, the methods described herein comprise a step of identifying or diagnosing a subject that is suffering a condition, for example, one or more types of cancer. As used herein the term "diagnose", "diagnosis", or "identify" of a condition includes predicting or diagnosing the condition, determining predisposition to the condition, monitoring treatment of the condition, diagnosing a therapeutic response of the disease and prognosis of the condition, condition progression, and response to particular treatment of the condition. For example, a human subject can be examined, or a blood sample obtained from the human subject can be assayed according to any of the methods described herein to determine the presence and/or quantity of markers of a condition or malignant cell type in the sample, thereby diagnosing or staging a condition or a cancer.

As previously noted, a subject that is suffering from cancer or under a cancer treatment can experience a decline of mental state or cognitive, learning, memory functions. Methods, kits, and/or compositions comprising magnesium threonate and/or the use of magnesium threonate described herein can be useful for purposes described herein, such as treating, supporting, maintaining, enhancing, and/or improving health, mental state, cognitive, learning, memory function, and/or another condition of a subject that is suffering from one or more types of cancer or under one or more cancer treatment. According to embodiments of the invention, a subject that is suffering from cancer or showing, exhibiting, displaying one or more cancer symptoms is first identified or diagnosed. Subsequent to identifying the subject suffering from one or more cancer, a composition comprising magnesium threonate is administered to the subject to improve the mental state of the subject. According to other embodiments of the invention, a composition comprising one or more anti-cancer agents and magnesium threonate is disclosed. A description of various aspects, features, embodiments, and examples, is provided herein.

Subject

The methods and compositions comprising magnesium threonate described herein can be used to treat a subject that is suffering from one or more types of cancer. The subject can be any subject that can be suffering from cancer, e.g., the subject can be a eukaryotic subject, such as an animal, e.g., a dog, a cat, a horse, a bird, a fish, a rabbit, a guinea pig, a sheep, a goat, a bovine, a chicken. In some embodiments, the subject can be cold-blooded animals, warm-blooded animals, mammals, domesticated mammals, or primates. In some cases, the subject can be a vertebrate animal, or a mammal, e.g., human.

The human subject can be of any age, including advanced age. The human subject can be a child (e.g., a neonate, an infant, a toddler, and a preadolescent), an adolescent, a pubescent, or an adult (e.g., an early adult, a middle aged adult, a senior citizen). The human subject can be between about 0 months and about 120 years old, or older. The human subject can be between about 0 and about 12 months old; The human subject can be between about 0 and 12 years old; The human subject can be between about 13 years and 19 years old; for example, about 13, 14, 15, 16, 17, 18, or 19 years old. The human subject can be between about 20 and about 39 year old; for example, about 20, 21, 22, 23, 24, 25, 26, 27, 28, 29, 30, 31, 32, 33, 34, 35, 36, 37, 38, or 39 years old. The human subject can be between about 40 to about 59 years old; for example, about 40, 41, 42, 43, 44, 45, 46, 47, 48, 49, 50, 51, 52, 53, 54, 55, 56, 57, 58, or 59 years old. The human subject can be greater than 59 years old; for example, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. The human subject can be about 45 years old or older. The human subject can be 55 years old or older. The human subjects can include male subjects and/or female subjects. In some cases, the human subject can be an individual or a patient to whom a composition is to be administered for experimental, diagnostic, nutritional, and/or therapeutic purposes. A subject or patient can be a subject or patient of normal, good, or excellent health, mental state, cognitive, and/or nutritional status, or of compromised health, mental state, cognitive, and/or nutritional status, including of abnormal, poor, damaged, unhealthy, impaired, diseased, and/or nutritionally deficient status.

Cancer Types

In some embodiments, methods of the present disclosure comprise administrating compositions that comprise magnesium threonate can be used to treat a subject that is suffering from one or more types of cancer. In some embodiments, the one or more types of cancer can be solid tumors or cystic tumors. In some embodiments, the solid tumors or cystic tumors can be at a benign, pre-malignant or malignant state. The one or more types of cancer that a subject can be suffering from include, but are not limited to, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, methods and composition comprising magnesium threonate described herein can be used to treat a subject that is suffering from solid tumors. Solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Cancer Diagnostic

A subject can be identified or diagnosed to be suffering from one or more types of cancer by one or more cancer diagnostics, and/or other examinations that are known in the medical art. To accurately identify a subject that is suffering from cancer, a complete evaluation of the medical history, physical examination of the subject along with one or more diagnostic or examination can be needed. One or more cancer diagnostics or examination can be performed to determine whether a subject is suffering from cancer, or if another condition such as an infection is mimicking the symptoms of cancer. Cancer diagnostics or examination can be used to confirm or eliminate the presence of a condition (e.g., cancer), monitor the condition process, perform prognosis of the condition, strategize cancer therapeutics and treatment, and evaluate the effectiveness of treatment for the subject. In some cases, diagnostics or examination can be repeated when a subject's condition has changed or is changing, if a biological sample collected from the subject is not of good enough quality, or an abnormal test result can need to be confirmed. Examples of cancer diagnostic or examination can include, but are not limited to, imaging, laboratory tests (including tests for tumor markers), tumor biopsy, endoscopic examination, surgery, or genetic testing.

A subject can be diagnosed or identified to be suffering from cancer by imaging. Imaging can be used to detect solid tumors, to detect abnormalities of body tissues, to determine the extent of disease, or to evaluate the effectiveness of treatment. Imaging can also be used concurrently with surgical procedures or to obtain biopsies. The types of imaging that can be used for cancer diagnosis to identify a subject suffering from cancer include: transmission imaging, reflection imaging, and/or emission imaging. Non-limiting examples of transmission imaging include: X-rays, computed tomography scans (CT scans), fluoroscopy, bone scan, lymphangiogram (LAG), and mammogram. Non-limiting examples of reflection imaging include ultrasound or sonography. Non-limiting examples of emission imaging include magnetic resonance imaging (MRI) and positron emission tomography (PET).

A subject can be diagnosed or identified to be suffering from cancer by performing laboratory tests on biological samples obtained from the subject. Laboratory test uses chemical or biochemical processes to measure levels of chemical or biological components in body fluids and tissues. The biological samples or specimens that can be used in laboratory tests include, but are not limited to, blood and urine. One or more types of chemical and biological components in the biological samples or specimens can be detected and measured using one or more tests. The chemical or biological components can include blood glucose, electrolytes, enzymes, hormones, lipids (fats), other metabolic substances, and proteins. Non-limiting examples of laboratory tests include blood tests, urinalysis, and tumor biomarker analysis.

Blood tests can include one or more different measurements or tests to check the levels of different substances in the blood specimen. Based on the levels of different substances measured, a condition such as cancer can be identified. The substances that can be measured include, but are not limited to, waste products such as creatinine or blood urea nitrogen (BUN), electrolytes that are critical to the body's healthy functioning, or a complete blood count. Blood tests can be coagulation studies, determining how quickly the blood clots. A blood test can also be a complete blood count (CBC). In a CBC, the size, number, and maturity of the different blood cells (e.g., red blood cells, white blood cells, platelets) in a specific volume of blood are measured. The hemoglobin portion of the CBC measures the oxygen carrying capacity of the red blood cells while the hematocrit measures the percentage of red blood cells in the blood.

Urinalysis can be performed to check for the presence and the level of drugs, blood, proteins, or other substances in the urine. Based on the abnormal presence or the level of substances in the urine, a condition such as cancer can be identified. Blood in the urine (hematuria) can be the result of a benign (noncancerous) condition. High levels of protein in the urine (proteinuria) can indicate a kidney or cardiovascular problem.

Tumor biomarkers in the biological samples or specimens of a subject can be measured to identify whether the subject is suffering from cancer. Tumor biomarkers can be substances that are released by cancer cells into the blood or urine. Tumor biomarkers can also be substances created by the body in response to cancer cells. Non-limiting examples of tumor biomarkers include prostate-specific antigen (PSA), prostatic acid phosphatase (PAP), CA 125, carcinoembryonic antigen (CEA), alpha-fetoprotein (AFP), human chorionic gonadotropin (HCG), CA 19-9, CA 15-3, CA 27-29, lactate dehydrogenase (LDH), and neuron-specific enolase (NSE).

A subject can be diagnosed or identified to be suffering from cancer by performing a tumor biopsy. During the tumor biopsy, biological samples or specimens such as a piece of tissue or cells are removed or harvested from the body of the subject for analysis in a laboratory. Gross morphology of the cells, immunohistochemistry, histology or polymerase chain reaction to measure gene expressions can be performed to identify cancerous origins. Non-limiting examples of a tumor biopsy include bone marrow biopsy, endoscopic biopsy (e.g., cytiscioy, bronchoscopy, colonscopy), needle biopsy (e.g., fine-needle aspiration, core needle biopsy, vacuum-assisted biopsy, image-guided biopsy, liver biopsy), skin biopsy (e.g., shave biopsy, punch biopsy, excisional biopsy, incisional biopsy) and surgical biopsy (e.g., incisional biopsy, excisional biopsy).

An endoscopic examination can be performed to diagnose or identify a subject suffering from cancer. An endoscopic examination is performed with an endoscope, which can be used to look into the esophagus, stomach duodenum, colon or rectum. An endoscope can also be used to take tissue from the body or to take color photographs of the inside of the body. Non-limiting examples of endoscopic examinations include colonoscopy, endoscopic retrograde cholangiopancreatography (ERCP), esophagogastroduodenoscopy (Also called EGD or upper endoscopy), sigmoidoscopy or cystoscopy (Also called cystourethroscopy).

Cancer Therapeutic

The current methods and compositions comprising magnesium threonate and/or the use of magnesium threonate can be used on a subject that is also treated with a cancer therapeutic. The cancer therapeutic can be a treatment that targets the specific type of cancer that the subject is suffering from. The types of cancer therapeutics that can be used on subject suffering from one or more types of cancer can be any cancer therapeutic that is well known in the medical art, as published by American Cancer Society on www.cancer.org/treatment/treatmentsandsideeffects/treatmenttypes/index, access on Jan. 31, 2013. Magnesium threonate can be administered to the subject that is suffering from one or more types of cancer when the subject is under cancer treatment or treated with a cancer therapeutic. The cancer therapeutic can be used to treat the subject together or separately with the administration of magnesium threonate. The subject can be treated with one or more cancer therapeutics together or separately.

The types of cancer therapeutics that can be given to a subject that is suffering from one or more types of cancer can be any cancer therapeutics that are well known in the art. Non-limiting examples of such cancer therapeutic include surgery, chemotherapy, radiation therapy, targeted therapy, immunotherapy, hyperthermia, stem cell transplant, photodynamic therapy, laser treatment or other alternative methods. Various agents, devices, or procedures can be used in combination in any of the cancer therapeutic treatment.

In some embodiments, the cancer therapeutic can be surgery. Surgery can be used to diagnose, treat, or even help prevent cancer in some cases. For example, identifiable solid tumors can be removed by surgery. In some embodiments, the cancer therapeutic can be chemotherapy. Chemotherapy or chemo is the use of one or more anti-cancer agents to treat cancer. The anti-cancer agents can be comprised in the same composition comprising magnesium threonate, or can be administered separately. The anti-cancer agents can treat cancer by interfering, inhibiting, promoting or being involved in various signaling pathways that are associated with cancer. In some embodiments, the cancer therapeutic can be radiation therapy. Radiation therapy uses high-energy particles or waves to destroy or damage cancer cells. It is one of the most common treatments for cancer, either by itself or along with other forms of treatment. In some embodiments, the cancer therapeutic can be targeted therapy. Targeted therapy is a newer type of cancer treatment that uses drugs or other substances to more precisely identify and attack cancer cells, usually while doing little damage to normal cells. In some embodiments, the cancer therapeutic can be immunotherapy. Immunotherapy is treatment that uses the body's own immune system to help fight cancer. In some embodiments, the cancer therapeutic can be hyperthermia, which is to deliver heat to treat cancer. In some embodiments, the cancer therapeutic can be stem cell transplant, such as peripheral blood bone marrow, and cord blood transplants. In some embodiments, the cancer therapeutic is photodynamic therapy. Photodynamic therapy or PDT is a treatment that uses special drugs, called photosensitizing agents, along with light to kill cancer cells. The drugs only work after they have been activated by lights at certain wavelengths. In some embodiments, the cancer therapeutic can be laser treatment. In some embodiments, the cancer therapeutic can be blood product donation and transfusion.

In some embodiments, the cancer therapeutic can be an alternative method for cancer management. The types of alternative methods for cancer management can be any type that is well known in the art (American Cancer Society, Complementary and Alternative Methods for Cancer Management, Published May 18, 2011). The alternative methods for cancer management can be used instead of mainstream cancer treatment. The alternative methods can be unproven, have not been scientifically tested, or have been disproved. The choice of alternative methods to treat a type of cancer may differ subject to subject, and can depend on the subject's own will or preferences. The alternative methods for cancer management can be acupuncture, aromatherapy, art therapy, biofeedback, labyrinth walking, massage therapy, meditation, music therapy, prayer and spirituality, Tai-chi, or yoga.

Anti-Cancer Agents

The methods and compositions comprising magnesium threonate described herein can also be used to treat a subject suffering from one or more cancers in conjunction with administering other well known anti-cancer agents or therapeutic agents that are selected for their particular usefulness against the cancer that is being treated. The anti-cancer or therapeutic agents can be other inhibitors of parts of the signaling pathway that link cell surface growth factor receptors to nuclear signals initiating cellular proliferation. In some embodiments, an effective amount of magnesium threonate can be administered to the subject in conjunction with one or more anti-cancer agents to support the cancer treatment with the one or more anti-cancer agents. The compositions comprising magnesium threonate described herein to be used to treat a subject that is suffering from cancer can further comprise one or more anti-cancer or therapeutic agents.

Such known anti-cancer and/or therapeutic agents that can be used in combination with magnesium threonate are described herein. The anti-cancer and/or therapeutic agents can include other antiproliferative/antineoplastic drugs and combinations thereof, cytostatic agents, anti-invasion agents, inhibitors of growth factor function, antiangiogenic agents, vascular damaging agents, endothelin receptor antagonists, antisense therapeutic agents, gene therapeutic agents, or immunotherapeutic agents.

The anti-cancer and/or therapeutic agents can be other antiproliferative/antineoplastic drugs or combinations thereof. Non-limiting examples include alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

The anti-cancer and/or therapeutic agents can be cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride.

The anti-cancer and/or therapeutic agents can be anti-invasion agents. Non-limiting examples of anti-invasion agents include c-Src kinase family inhibitors like 4-(6-chloro-2,3methylenedioxyanilino)-7-[2-(4-methylpiperazin-1-yl)ethoxy]-5-tetrahydropyran-4yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS-354825; J. Med. Chern., 2004, 47, 66586661) and bosutinib (SKl-606), and metalloproteinase inhibitors like marimastat, inhibitors of urokinase plasminogen activator receptor function or antibodies to Heparanase.

The anti-cancer and/or therapeutic agents can be inhibitors of growth factor function. Non-limiting examples of the inhibitors include growth factor antibodies and growth factor receptor antibodies (such as the anti-erbB2 antibody trastuzumab [Herceptin™], the anti-EGFR antibody panitumumab, the anti-erbB 1 antibody cetuximab [Erbitux, C225] and any growth factor or growth factor receptor antibodies disclosed by Stem et al. Critical reviews in oncology/haematology, 2005, Vol. 54, pp 11-29), tyrosine kinase inhibitors (for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy) quinazolin-4-amine (erlotinib, OSI-774) and 6-acrylamido-N-(3-chloro-4-fluorophenyl)-7-(3- morpholinopropoxy)-quinazolin-4-amine (CI 1033), erbB2 tyrosine kinase inhibitors such as lapatinib), inhibitors of the hepatocyte growth factor family, inhibitors of the insulin growth factor family, inhibitors of the platelet-derived growth factor family such as imatinib and/or nilotinib (AMN107), inhibitors of serine/threonine kinases (for example Ras/Raf signaling inhibitors such as farnesyl transferase inhibitors, for example sorafenib (BAY 43-9006), tipifarnib (RI15777) and lonafarnib (SCH66336)), inhibitors of cell signaling through MEK and/or AKT kinases, c-kit inhibitors, abl kinase inhibitors, P13 kinase inhibitors, Plt3 kinase inhibitors, CSF-IR kinaes inhibitors, IGF receptor (insulin like growth factor) kinase inhibitors, aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors.

The anti-cancer and/or therapeutic agents can be antiangiogenic agents such as those which inhibit the effects of vascular endothelial growth factor. Non-limiting examples include the anti-vascular endothelial cell growth factor antibody bevacizumab (Avastin™) and a VEGF receptor tyrosine kinase inhibitor such as vandetanib (ZD6474), vatalanib (PTK787), sunitinib (SU11248), axitinib (AG-013736), pazopanib (GW 786034) and 4•{4-fluoro-2-methylindo1-5-yloxy)-6-methoxy-7-(3pyrrolidin-1-ylpropoxy)quinazoline (AZD2l7l; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin.

The anti-cancer and/or therapeutic agents can be vascular damaging agents such as Combretastatin A4 and compounds disclosed in International Patent Applications WO 99/02166, WO 00/40529, WO 00/41669, WO 01/92224, WO 02/04434 and WO 02/08213.

The anti-cancer and/or therapeutic agents can be an endothelin receptor antagonist, for example zibotentan (ZD4054) or atrasentan.

The anti-cancer and/or therapeutic agents can be any agent that is used in antisense therapies, for example those which are directed to the targets listed above, such as ISIS 2503, an anti-ras antisense.

The anti-cancer and/or therapeutic agents can be any agent that is used in gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy.

The anti-cancer and/or therapeutic agents can be any agent that is used in immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies.

In certain embodiments, the therapeutic agent can be selected from pacliataxel, bortezomib, dacarbazine, gemcitabine, trastuzumab, bevacizumab, capecitabine, docetaxel, erlotinib, aromatase inhibitors, such as AROMASIN™ (exemestane), and estrogen receptor inhibitors, such as FASLODEX™ (fulvestrant).

Anti-Cancer Diets and Supplements

The methods and compositions comprising magnesium threonate can be useful in combination with one or more agents that are used as supplements. In some embodiments, an effective amount of magnesium threonate can be administered to the subject in conjunction with one or more supplements that can be used in a cancer therapy. In some cases, the supplements can have anti-cancer effects. The composition comprising magnesium threonate can also comprise one or more supplements that can have anti-cancer effects. The composition comprising magnesium threonate can also be used in conjunction with a nutritional diet that can have anti-cancer effects.

Such known supplements or diets with anti-cancer effects that can be used in combination with magnesium threonate are described herein. Diets or supplements that can be beneficial in supporting, ameliorating or treating a subject suffering from cancer can be used in conjunction with magnesium threonate. Such diet can be found in Donaldson, Nutrition and cancer: A review of the evidence for an anti-cancer diet, Nutrition Journal 2004, 3:19. The diet can be a reduced intake of calories, a reduced intake of refined sugar, an increased fiber intake, a reduced intake of red meat, a higher omega 3:6 ratio, flax seed, or an increased intake of fruits and vegetables such as cruciferous vegetables. The supplements that can be administered to a subject suffering from cancer in conjunction with magnesium threonate can be a various herbs, vitamins, minerals and the like. Non-limiting examples of such supplements include: aloe, arnica, astragalus, aveloz, black cohosh, black walnut, bromelain, calcium, capsicum, cat's claw, celandine, cesium chloride, chamomile, chaparral, Chinese herbal medicine, chlorella, cloves, comfrey, copper, Echinacea, eluthero or Siberian ginseng, enercel, essiac tea, evening primrose, folic acid, germanium, ginger, ginkgo, ginseng, goldenseal, gotu kola, hozsey herbal treatment, Indian snakeroot, kava, licorice, marijuana, milk thistle, mistletoe, molybdenum, mugwort, oleander leaf, orthomolecular medicine, pau d'arco, PC-SPES, PC-HOPE, PC-CARE, peppermint, phytochemicals, pine bark extract, pokeweed, potassium, red clover, saw palmetto, selenium, sodium bicarbonate, St. John's wort, strychnos Nux-vomica, tea tree oil, thuja, turmeric, valerian, venus flytrap, vitamin A, retinoids, provitamin A carotenoids, vitamin B complex, vitamins C, D, E, and K, white birch, wild yam, wormwood, yohimbe, zinc, chlorophyll, co-enzyme Q10, antioxidants (such as alpha- and beta-carotene and other carotenoids, lycopene, melatonin), grape seed extract (or proanthocyanidin), green tea extract (or flavanol or epigallocatechin-3-gallate (EGCG)), probiotics, oral digestive enzyme supplements (such as trypsin, papin, or chymotrypsin), garlic, L-glutamine, iron, mushroom, or a combination thereof.

Other Conditions

A method described herein comprising the use of a magnesium threonate composition can be used on a subject that is suffering from cancer and another condition. The subject that is suffering from cancer can be suffering from another condition that would result in decline of mental state of the subject. The condition that the subject can be suffering from can include depression, anxiety, dementia, insomnia, cognitive impairment, memory function decline, learning capacity decline, mood swing, attention deficit hyperactivity disorder, magnesium deficiency, mild cognitive impairment, Alzheimer's disease, Huntingdon's disease, autism, schizophrenia, cognitive decline as secondary effect of disease or medical treatment (HIV disease, cancer, chemotherapy), ALS, Parkinson's disease, diabetes, cardiovascular disease (e.g., hypertension), glaucoma, migraine, delirium, delusion, hallucination, disseminated systemic metastases, confusion, agitation, disorientation, reduced consciousness, perceptual disturbance, change in psychomotor activity, lateralizing sign, seizure, merely by way of example. The subject that is suffering from cancer can also suffer loss of appetite, nausea, vomiting, fatigue, seizures, abnormal heart rhythms, diabetes, and/or cardiovascular disease.

Combination Treatment

The methods described herein comprise administering the compositions comprising magnesium threonate to a subject for a period of time. The compositions can be administered to a subject for the same duration of time as an anti-cancer treatment or a cancer therapeutic treatment. The composition can be administered for a different duration of time from the anti-cancer treatment or the cancer therapeutic treatment. For example, the magnesium threonate may be administered for 30 days while the anti-cancer treatment is administered for 6 months. The subject can be on an anti-cancer treatment for a period of time before administering the composition comprising magnesium threonate. The subject can stop the administration of magnesium threonate composition before the end of an anti-cancer treatment.

The methods described herein can comprise administering a composition comprising magnesium threonate in conjunction with administering one or more anti-cancer agents or a cancer therapeutic. In some embodiments, the compositions comprising magnesium threonate may be administered together with the anti-cancer agents or the cancer therapeutic at the same time in the same route. In some embodiments, the composition comprising magnesium threonate may be administered separately from the anti-cancer therapeutic agents or cancer therapeutic. In some embodiments, the composition comprising magnesium threonate and the anti-cancer agents and/or cancer therapeutic may be administered sequentially, with the anti-cancer agents or cancer therapeutic first or the magnesium threonate first. In some embodiments, the composition comprising magnesium threonate may be administered to a subject in conjunction with one or more anti-cancer agents or a cancer therapeutic. In some embodiments, the composition comprising magnesium threonate may be administered at the same administration route with the anti-cancer agents or the cancer therapeutic. The composition comprising magnesium threonate may be administered at a different administration route with the anti-cancer agents or the cancer therapeutic. For example, the composition comprising magnesium threonate may be administered orally while the anti-cancer agents may be administered via intravenous injection.

In some cases, the subject in need thereof may be administered both one or more anti-cancer agents and a cancer therapeutic. Each of the anti-cancer agents can be administered via the same or different administration routes. The one or more anti-cancer agents can be administered via the same or different administration routes. Each of the anti-cancer agents can be administered for the same or different treatment duration. The one or more anti-cancer agents can be administered for the same or different treatment duration. Each of the anti-cancer agents can be administered at the same or different time. The one or more anti-cancer agents can be administered at the same or different time.

Course of Treatment

In some embodiments, the methods and compositions comprising magnesium threonate described herein can be administered once or more than once to a subject suffering from cancer. The subject can be administered magnesium threonate about once, twice, three times, four times, five times, six times, or more than six times per day. Administration of magnesium threonate can be about once a month, once every two weeks, once a week, or once every other day. In another embodiment magnesium threonate and one or more anti-cancer agents can be administered together about once per day to about 6 times per day. In another embodiment, the administration of magnesium threonate and one or more anti-cancer agents continues for less than about 7 days. In another embodiment, the administration of magnesium threonate can continue for more than about 7 days. In yet another embodiment the administration continues for equal or more than about 6, 7, 8, 9, 10, 11, 12, 13, 14, 15, 16, 17, 18, 19, 20, 21, 22, 23, 24, 25, 26, 27, 28, 29, 30 days, 2, 3, 4, 5, 6, 7, 8, 9, 10, 11, 12 months, 2, 3, 4, 5, 6, 7, 8, 9, 10, 11, 12, 13, 14, 15, 16, 17, 18, 19, 20, 21, 22, 23, 24, 25, 26, 27, 28, 29, 30 years. In some cases, continuous administration is achieved and maintained as long as necessary. In some embodiments, the composition comprising magnesium threonate is administered for at least about a month. In some embodiments, the composition is administered for at least about 1 week. In some embodiments, magnesium threonate is administered chronically on an ongoing basis.

The composition comprising magnesium threonate can be administered to a subject at any time of the day. For example, after meal, before meal, before sleep, after sleep, in the morning, in the afternoon, in the evening, and the like.

The composition comprising magnesium threonate can be administered to a subject that is suffering from different stages of cancer. Stage of cancer describes the severity of a subject's cancer based on the extent of the original (primary) tumor and whether or not cancer has spread in the body. The stages of the cancer can be determined by the TNM system, wherein the TNM system is based on the extent of the tumor (T), the extent of spread to the lymph nodes (N), and the presence of distant metastasis (M), according to National Cancer Institute, USA. The cancer that the subject is suffering from can be at stage 0, I, II, III, or IV. The cancer can be at metastasis.

Magnesium Threonate Composition

A composition appropriate for administration to a subject suffering from one or more types of cancer can comprise magnesium threonate, in which each magnesium cation is associated with two threonate anions. Such a composition can be prophylactically and/or therapeutically suitable or beneficial. Threonate is a natural metabolic product of vitamin C or ascorbic acid that can be associated with non-toxicity in animals (Thomas et al, Food Chem. 17, 79-83 (1985)) and biological benefit, such as the promotion of vitamin C uptake, in animals (Verlangieri et al., Life Sci. 48, 2275-2281 (1991)).

Magnesium has been shown to be involved in the cellular and molecular processes of organization of neural circuits in storage of information (Slutsky et al., Neuron, 44, 835-849 (2004)). It has been reported that supplementing the diet of aging rats with magnesium appears to increase the expression level of a particular brain molecule, the NMDA receptor, an effect associated with improvement of cognitive function (U.S. Patent Application Publication No. US 2006/0089335 A1). According to several studies, magnesium deficit can lead to or can be associated with attention deficit hyperactivity disorder (ADHD) in children and symptoms associated therewith (Kozielec et al., Magnes. Res. 10(2), 143-148 (1997) and Mousain-Bosc et al., Magnes. Res. 19(1), 46-52 (2006)). Magnesium supplementation can also improve many pathological symptoms, such as loss of appetite, nausea, vomiting, fatigue, seizures, abnormal heart rhythms, diabetes, and/or cardiovascular disease, for example.

Magnesium threonate can be suitable for relatively rapid magnesium intake, provision, and/or supplementation, as can be suitable or beneficial for any of a variety of applications, such as a nutritional or prophylactic application, and/or a therapeutic application. Magnesium threonate can be a suitable or beneficial vehicle for magnesium intake, provision, and/or supplementation application(s), such as any that can be accomplished via a dietary vehicle or a consumable vehicle, such as a magnesium-fortified food and/or a magnesium-fortified beverage, for example.

The compositions described herein can be pharmaceutical compositions comprising magnesium threonate and one or more anti-cancer agents. The composition can be formulated in various forms, dosages or packages that are intended for different administration routes. For example, the composition can be formulated in a solid or liquid dosage form. A description of various aspects, features, embodiments, and examples, is provided herein.

Forms

A composition comprising magnesium threonate appropriate for administration to a subject can be provided in any suitable form, such as a liquid form, a gel form, a semi-liquid (for example, a liquid, such as a viscous liquid, containing some solid) form, a semi-solid (a solid containing some liquid) form, and/or a solid form, for example. In some embodiments, the composition can be a solid or liquid pharmaceutical composition suitable for oral consumption. In some embodiments, compositions of the invention suitable for oral administration are presented as discrete dosage forms, such as a cachet, a tablet, a capsule, a pill, an emulsion, a gel, a plurality of beads encapsulated in a capsule, a powder, a suspension, a liquid, a semi-liquid, a semi-solid, a syrup, a slurry, a chewable, a non-chewable, a food or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. The composition can be a dietary supplement, a food form, or contained in a foodstuff. A food form can take the form of a food bar, a cereal product, a bakery product, a dairy product, and/or the like, for example. A bakery product form can take the form of a bread-type product, such as a bagel or bread itself, for example, a donut, a muffin, and/or the like, merely by way of example. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

A composition comprising magnesium threonate can employ a slow- or sustained-release form, a non-slow- or non-sustained-release from, and/or the like. Gradual-release tablets are known in the art. Examples of such tablets are set forth in U.S. Pat. No. 3,456,049. Such a composition can comprise an additional agent or agents, whether active or passive. A slow- or sustained-release form can delay disintegration and/or absorption of the composition and/or one or more component(s) thereof over a period, such as a relatively long period, for example.

The composition can be formulated in different forms according to the administration route that is intended to delivery therethrough. The subject pharmaceutical composition can, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. A pharmaceutical composition can be in unit dosage forms suitable for single administration of precise dosages. A pharmaceutical composition can include a conventional pharmaceutical carrier or excipient and a compound of the invention as an active ingredient. In addition, it can include other medicinal or pharmaceutical agents, carriers, adjuvants, etc. A magnesium threonate composition in a liquid form can be used in any suitable manner. In some embodiments, the magnesium threonate composition can be used as a beverage, such as a milk-based beverage, a sports drink, a fruit juice drink, an alcoholic beverage, and/or the like. In other embodiments, the magnesium threonate composition in liquid form contains multiple magnesium threonate compounds. In such embodiments, the weight percentage of each magnesium threonate compound can vary in relation to the other. In still other embodiments, the magnesium threonate composition in a liquid form can take the form of a magnesium-fortified product comprising water, magnesium threonate, and optionally, at least one agent sufficient to confer a suitable property to the product. In still another embodiment, a magnesium threonate composition in a liquid form can be formulated from a dry mix, such as a dry beverage mix or a magnesium-fortified, milk-comprising powder. A dry mix can be suitable in terms of transportation, storage, and/or shelf life. The composition can be formulated from the dry mix in any suitable manner, such as by adding a suitable liquid (e.g., water, milk, fruit juice, alcohol, etc.).

Dosage

In some embodiments, compositions are administered in dosages. It is known in the art that due to intersubject variability in compound pharmacokinetics, individualization of dosing regimen is necessary for optimal therapy. Dosing for magnesium threonate and the anti-cancer agents can be found by routine experimentation in light of the instant disclosure.

Determining an appropriate dosage for administration of a magnesium threonate composition to a subject can take into account any of a variety of factors, such as those just mentioned, for example, any potential or actual side-effect(s), and/or a purpose of the administration of the magnesium threonate composition, such as a nutritional or prophylactic purpose, a mental state maintenance or enhancement purpose, a disease or pathological condition treatment purpose, and/or other purpose(s) for which the magnesium threonate composition can be administered to a subject that is suffering from one or more types of cancer. Determining an appropriate dosage can take into account any of these factors, any other suitable factor(s), any side-effect(s), animal study modeling, human study modeling, clinical study modeling, drug study modeling, and any balancing therebetween.

In some embodiments, the magnesium threonate composition is in a single or unit dosage form. In some cases, the magnesium threonate composition can be in multiple dosage forms. The magnesium threonate compositions can be administered in a single dose or multiple doses.

It is contemplated that a dosage for administration of a magnesium threonate composition to a subject can be from about 1.5 mg/kg of body weight/day to about 18 mg/kg of body weight/day. For example, it is contemplated that a dosage for administration of a magnesium threonate composition to a subject can be from about 1.5 mg/kg of body weight/day to about 9 mg/kg of body weight/day of magnesium threonate compound for nutritional and/or prophylactic purpose(s); can be about 6 mg/kg of body weight/day to about 18 mg/kg of body weight/day of elemental magnesium or magnesium threonate compound for mental state maintenance and/or enhancement purpose(s); and can be about 9 mg/kg of body weight/day to about 18 mg/kg of body weight/day of elemental magnesium or magnesium threonate compound for cancer and/or pathological condition treatment purpose(s), such as the anti-cancer treatment. Such amounts can be suitable for a human subject, for example. In some embodiments, the dosage can be less than 1.5 mg/kg of body weight/day. In some embodiments, the dosage can be more than 18 mg/kg of body weight/day.

As mentioned above, such a dosage can be determined, modified and/or refined based on any suitable factor(s), such as results of clinical trials concerning subjects, for example human subjects. In some embodiments, a suitable dosage can be determined, modified and/or refined based on a determination of a suitable dosage for a suitable animal model, based on experimental studies or tests, for example, and conversion of such a suitable animal dosage to a suitable human dosage, based on suitable conversion factor(s), such as any suitable established conversion factor(s), for example. Further by way of example, it is contemplated that any such suitable human dosage can be further determined, modified and/or refined based on clinical trials involving human subjects, for example. The dosage can be determined according to the intended administration route.

In some embodiments, the concentration of a magnesium threonate compound provided in a composition in accordance with the present invention can be less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of magnesium threonate in the compositions can be greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125% , 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the amount of magnesium threonate compound or elemental magnesium in the composition can be equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g. In some embodiments, the amount of magnesium threonate compound or elemental magnesium in the composition is less than 1.5 g.

In some embodiments, the amount of magnesium threonate compound or elemental magnesium is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g. In some embodiments, the amount of magnesium threonate compound or elemental magnesium in the composition is more than 0.01 g.

In some embodiments, the amount of magnesium threonate is in the range of 0.00005-5 g, 0.0001-4 g, 0.0005-3 g, 0.001-2.5 g, 0.005-2 g, or 0.01-1.5 g.

In some embodiments, the magnesium threonate is effective over a wide dosage range. For example, in the treatment of adult humans, dosages from 0.0005 to 3 g, from 0.001 to 2.5 g, from 0.005 to 2 g per day, and from 0.01 to 1.5 g per day are examples of dosages that can be used. The exact dosage will depend upon the route of administration, the form in which the compound is administered, the subject to be treated, the body weight of the subject to be treated, the type of anti-cancer agent to be accompanied and the preference and experience of the attending physician.

Effective Amount of Magnesium Threonate

The amount of magnesium threonate in a composition that is needed to produce a physiological effect in a subject can be determined by various methods. One example of such method can comprise the steps of: a. obtaining a sample of biological fluid from the subject; and b. calculating the amount of magnesium to be supplied to said subject according to the formula of: $Mg_x = GFR \cdot T \cdot Mg_{mw} \cdot k_e ([Mg]_o^2 - [Mg]_o^1)/k_x$ wherein $Mg_x$ is effective amount of magnesium to be supplied to said subject; wherein $[Mg]_o^1$ is the initial concentration of magnesium in extracellular compartment; wherein $K_x$ is bioavailability of said magnesium threonate composition; wherein GFR is glomerular filtration rate; wherein $k_e$ is the excretion rate of filtered Mg in kidney; wherein T is time in hours; wherein $Mg_{mw}$ is molecular weight of the element magnesium; and wherein $[Mg]_o^2$ is a desired concentration of magnesium to be achieved upon supplementing said subject the determined amount of magnesium threonate composition.

The composition and/or the methods of use described herein can be effective or useful for maintaining, enhancing, and/or improving health, nutrition, mental state and/or another condition of a subject, such as cognitive, learning, and/or memory function, for example, in addition to cancer. The magnesium threonate can be present in an amount effective in the composition administered to a subject in improving the mental state or conditions that are associated with the decline of the mental state, for example, depression, anxiety, dementia, insomnia, cognitive impairment, memory function decline, learning capacity decline, mood swing, attention deficit hyperactivity disorder, magnesium deficiency, mild cognitive impairment, Alzheimer's disease, Huntingdon's disease, autism, schizophrenia, ALS, Parkinson's disease, glaucoma, migraine, delirium, delusion, hallucination, disseminated systemic metastases, confusion, agitation, disorientation, reduced consciousness, perceptual disturbance, change in psychomotor activity, lateralizing sign, seizure, and the like. The magnesium threonate can be present in an amount effective in the composition administered to a subject in improving the mental state of cognitive function as secondary effects of other conditions or medical treatments such as HIV, renal disease, diabetes, cardiovascular diseases, and the like. The amount of magnesium threonate can be effective in improving the cognitive functions of the subject being administered. For example, enhancing any aspect of such a process, such as learning, the performance of mental operations, the storage, retrieval, and/or use of information and/or thoughts, memory, and/or preventing a decline of a subjects cognitive state, for example. The magnesium threonate composition can be in an amount effective in improving other conditions that are also related to decline of cognitive functions such as hypertension, attention deficit hyperactivity disorder, Alzheimer's disease or Parkinson's disease.

Also provided is a method of treating a subject suffering from cancer and/or supporting an anti-cancer treatment of a subject comprising administering an effective amount of magnesium threonate to increase a physiological concentration of elemental magnesium as compared to an initial level of elemental magnesium prior to said administration. The physiological concentration can be the concentration in body fluid. The body fluid can be serum, plasma, or cerebrospinal fluid. A number of methods have been used to assess the body magnesium levels in humans. These methods differ from one another in the type of sample and the analytical technique used. Serum and plasma have been the two most commonly used types of samples although some studies used red blood cells or tissue samples. Among the Mg detection techniques used are: absorbance-based dye technique, atomic absorption technique, ion-selective electrode technique and NMR technique. The first two techniques measure the total magnesium concentration, which include both ionized free $Mg^{2+}$ and $Mg^{2+}$ bound to proteins and other molecules in the sample, while the latter two techniques measure only ionized magnesium.

In some cases, the increase in the elemental magnesium in body fluid is by at least about 1%, 2%, 3%, 4%, 5%, 6%, 7%, 8%, 9%, 10%, 11%, 12%, 13%, 14%, 15%, 16%, 17%, 18%, 19% or 20%. In some cases, the increase is by at least about 10%. In some cases, the increase is by at least about 5%. Where desired, suitable concentrations for eliciting the effects of magnesium supplementation as described herein can be from about 0.8, 0.9, 1.0, 1.1, 1.2, 1.3, 1.4, 1.5, 1.6, times the median value reported.

In another aspect, the administration of the magnesium threonate composition can yield a level of physiological concentration of magnesium sustained at the level of 0.75 mM or above for at least about 15 days. In some instances, the magnesium is sustained at the level of 0.75 mM or above for at least about one month or at least about four months. Where desired, one can administer to a subject an amount of magnesium threonate that is effective to achieve a physiological concentration of magnesium at about 0.75 mM, 0.78 mM, 0.8 mM, 0.82 mM, 0.84 mM, 0.86 mM, 0.88 mM, 0.90 mM, 0.92 mM, 0.94 mM, 0.96 mM, 0.98 mM, or above. In some embodiments, these concentrations are "high end" concentrations. Such "high end" concentrations include serum magnesium concentration from about 0.60 mM, 0.65 mM, 0.70 mM, 0.75 mM, 0.80 mM, 0.85 mM, 0.95 mM, 1.0 mM, 1.05 mM, 1.10 mM, 1.15 mM to 1.2 mM or even higher, plasma magnesium concentration from about 0.70 mM, 0.75 mM, 0.80 mM, 0.85 mM, 0.95 mM, 1.0 mM, to 1.05 mM or even higher, and/or blood ionized magnesium concentration from about 0.50 mM, 0.55 mM, 0.60 mM, 0.65 mM, to about 0.70 mM.

In one aspect, such magnesium concentration is maintained for at least 1 week, 2 weeks, 3 weeks, 1 month, 2 months, 3 months, 4 months, 5 months, 6 months, 1 year, 1.5 years, 2 years, or even longer. Preferably, the concentration of magnesium is measured under a fasting condition, e.g., after fasting or without taking food for at least about 8 hours, 10 hours, 12 hours, 15 hours, 24 hours, or even longer.

The physiological concentration of magnesium can be serum concentration, plasma concentration, or cerebrospinal fluid concentration. Such physiological concentration can be determined by measuring intracellular ionized magnesium in red blood cells, bone magnesium content, magnesium concentration in the cerebrospinal fluid, a sublingual magnesium assay intracellular free magnesium, or nuclear magnetic resonance spectroscopy.

Administration Route

A magnesium threonate composition appropriate for administration to a subject can be administered in any suitable manner. Such administration can be oral and/or any other suitable administration, such as transdermal, intravenous injection, intraarterial injection, inhalation, aerosol, intramuscular injection, vaginal, rectal, subdermal, sublingual, parenteral, ophthalmic, pulmonary, transmucosal, otic, nasal insufflation, pharyngeal administration and topical administration. Components of a magnesium threonate composition, such as magnesium threonate and one or more anti-cancer agents can be administered to a subject concurrently, such as in any manner of concurrent administration described herein and/or in U.S. Patent Application Publication No. US 2006/0089335 A1. In addition, by way of example only, parenteral delivery includes intramuscular, subcutaneous, intravenous, intramedullary injections, as well as intrathecal, direct intraventricular, intraperitoneal, intralymphatic, and intranasal injections.

Pharmaceutical Compositions and Administration

A magnesium threonate composition can be a formulated to provide an effective amount of magnesium threonate as the active ingredient, or a pharmaceutically acceptable salt, ester, prodrug, solvate, hydrate or derivative thereof. The magnesium threonate composition can be a pharmaceutical composition. The magnesium threonate composition can further comprise one or more anti-cancer agents that are selected for their particular usefulness against the cancer that is being treated. The anti-cancer agents can be in an amount effective in treating a symptom associated with the cancer, such as improving the mental state of a subject that is suffering one or more types of cancer and has impaired mental state due to cancer or cancer treatment. The composition can also be formulated to provide an effective amount of pharmaceutically active agents (e.g., anti-cancer agents) and an excipient. In some embodiments, the magnesium threonate can be present in the composition as an excipient. Where desired, the compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject compositions comprising magnesium threonate and one or more anti-cancer agents can be administered alone or in combination with one or more other agents, which are also typically administered in the form of compositions. Where desired, magnesium threonate, one or more anti-cancer agents and other agent(s) can be mixed into a preparation. In some embodiments, the magnesium threonate, one or more anti-cancer agents or other agents can be formulated into separate preparations or packaged separately to use them in combination. In some embodiments, the magnesium threonate and the one or more anti-cancer agents can be used separately or at the same time. In some embodiments, the compositions can be in unit dosage form.

A composition of the invention typically comprises an active ingredient (e.g., magnesium threonate or anti-cancer agent) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants. The composition can further comprise one or more supplements or other active ingredients. The composition can further comprise one or more herbal extract.

Described below are non-limiting exemplary compositions and methods for preparing the same.

In some embodiments, the invention provides a pharmaceutical composition for oral administration comprising magnesium threonate, and a pharmaceutical excipient suitable for oral administration. In some embodiments, the invention provides a solid or liquid pharmaceutical composition for oral administration comprising: (i) an effective amount of magnesium threonate; (ii) an effective amount of one or more anti-cancer agents; optionally (iii) an effective amount of one or more other agents; and (iv) a pharmaceutical excipient suitable for oral administration.

This invention further encompasses anhydrous pharmaceutical compositions and dosage forms comprising an active ingredient, since water can facilitate the degradation of some compounds. For example, water can be added (e.g., 5%) in the pharmaceutical arts as a means of simulating long-term storage in order to determine characteristics such as shelf-life or the stability of formulations over time Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, milk, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in compositions of the invention to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono-and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/ diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition can include a solubilizer to ensure good solubilization and/or dissolution of compounds of the present invention and to minimize precipitation of such compounds. This can be especially important for compositions for non-oral use, e.g., compositions for injection. A solubilizer can also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG ; amides and other nitrogen-containing compounds such as 2-pyrrolidone, 2-piperidone, $\epsilon$-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, $\delta$-valerolactone and isomers thereof, $\beta$-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer can also be used, such as 5%, 2%, 1% or even less. Typically, the solubilizer can be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base can be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In some embodiments, the invention provides a pharmaceutical composition for injection containing a compound of the present invention and a pharmaceutical excipient suitable for injection. Components and amounts of agents in the compositions are as described herein.

Example forms in which compositions of the present invention can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions can be prepared by incorporating a compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. Preferably the compositions are administered by the oral or nasal respiratory route for local or systemic effect. Compositions in preferably pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can be administered, preferably orally or nasally, from devices that deliver the formulation in an appropriate manner.

Pharmaceutical compositions can also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

The composition can further comprise one or more herbal extract or supplements that are known in the art. Non-limiting examples of the herbs or the supplements can be Acai, Alfalfa, Aloe, Aloe Vera, Aristolochic Acids, Asian Ginseng, Astragalus, Bacillus coagulans, Belladonna, Beta-carotene, Bifidobacteria, Bilberry, Bilberry, Biotin, Bitter Orange, Black Cohosh, Black Cohosh, Black psyllium, Black tea, Bladderwrack, Blessed thistle, Blond psyllium, Blueberry, Blue-green algae, Boron, Bromelain, Butterbur, Calcium, Calendula, Cancell/Cantron/Protocel, Cartilage (Bovine and Shark), Cassia cinnamon, Cat's Claw, Chamomile, Chasteberry, Chondroitin sulfate, Chromium, Cinnamon, Clove, Coenzyme Q-10, Colloidal Silver Products, Cranberry, Creatine, Dandelion, Dandelion, Devil's claw, DHEA, Dong quai, Echinacea, Ephedra, Essiac/Flor-Essence, Eucalyptus, European Elder (Elderberry), European Mistletoe, Evening Primrose Oil, Fenugreek, Feverfew, Fish oil, Flaxseed, Flaxseed oil, Folate, Folic acid, Garlic, Ginger, Gingko, Ginseng, Glucosamine hydrochloride, Glucosamine sulfate, Goldenseal, Grape Seed Extract, Green Tea, Hawthorn, Hoodia, Horse Chestnut, Horsetail, Hydrazine Sulfate, Iodine, Iron, Kava, Lactobacillus, Laetrile/Amygdalin, L-arginine, Lavender, Licorice, Lycium, Lycopene, Magnesium, Manganese, Melatonin, Milk Thistle, Mistletoe Extracts, Niacin and niacinamide (Vitamin B3), Noni, Oral Probiotics, Pantothenic acid (Vitamin B5), Passionflower, PC-SPES, Pennyroyal, Peppermint, Phosphate salts, Pomegranate, Propolis, Pycnogenol, Pyridoxine (Vitamin B6), Red Clover, Red yeast, Riboflavin (Vitamin B2), Roman chamomile, Saccharomyces boulardii, S-Adenosyl-L-Methionine (SAMe), Sage, Saw Palmetto, Selected Vegetables/Sun's Soup, Selenium, Senna, Soy, St. John's Wort, sweet orange essence, Tea Tree Oil, Thiamine (Vitamin B1), Thunder God Vine, Turmeric, Valerian, Vitamin A, Vitamin B12, Vitamin C, Vitamin D, Vitamin E, Vitamin K, Wild yam, Yohimbe, Zinc or 5-HTP.

When the magnesium threonate is administered in a composition that comprises one or more anti-cancer agents, and the anti-cancer agents have a shorter half-life than the magnesium threonate unit dose forms of the anti-cancer agent and the magnesium threonate can be adjusted accordingly.

Applications

A magnesium threonate composition appropriate for administration to a subject suffering from one or more types of cancer can be useful in therapeutic applications and/or nutritional applications. A nutritional application can refer to an application suitable for warding off and/or preventing pathological conditions that are associated with cancer and/or subject to treatment with magnesium. A nutritional application can refer to an application suitable for maintaining and/or enhancing physiological function, such as physiological function at a state considered normal. A mental state, such as the mood, for example, of a subject that is suffering from cancer can be maintained and/or enhanced by administering a suitable magnesium threonate composition. A therapeutic application includes, but is not limited to, treating pathological conditions that are associated with cancer and/or subject to treatment with magnesium.

A magnesium threonate composition can be used to at least maintain and/or to enhance mental state and/or cognitive function of a subject suffering from one or more types of cancer. In such a composition, an amount of magnesium, or an effective amount of same, associated with at least one magnesium threonate composition can be sufficient for any suitable function described herein. For example, a concentration of elemental magnesium associated with at least one threonate of such a composition in a liquid form (e.g., an aqueous solution) can be from about 5 mg/L to about 12 g/L, such as from about 50 mg/L to about 12 g/L, for example.

A magnesium threonate composition can be used for treating other conditions that are associated with decline of mental state, for example: MCI, AD, and/or any other suitable malady or disease of a subject that is suffering from one or more types of cancer. In such a composition, an amount of magnesium, or an effective amount of same, associated with at least one magnesium threonate composition can be sufficient for any suitable function described herein. It is contemplated that a magnesium threonate composition described herein can be administered to a human subject to suitable or beneficial effect, such as nutritional, prophylactic, and/or therapeutic effect, for example, as can be useful to address the mental state of the subject, for example, in any suitable manner. In some embodiments, a magnesium threonate composition of the present invention can be administered to a human subject susceptible to, or afflicted by, depression and/or mood swing to suitable or beneficial effect. In other embodiments a magnesium threonate composition can be administered to a human subject for a variety of useful purposes, such as the maintenance, enhancement, and/or improvement of cognitive function, mental state, learning, memory, mood, anxiety, depression, migraine, and/or other conditions. As the magnesium threonate composition comprises an endogenous mineral, magnesium, and possibly other natural ingredients, such as an enhancing agent described herein, for example, in some embodiments administration of a magnesium threonate compound of the present invention can be safe over a relatively long term. In still other embodiments, administration of such a magnesium threonate compound or composition occurs over a long-term period. For example, a subject can be administered a compound and/or composition of the present invention for weeks, months, years, and/or for life. Such long-term administration can be used for supporting, maintaining or enhancing the mental state of the subject while the subject is suffering from cancer. These examples are not limiting examples, as long-term administration of the magnesium threonate compounds of the present invention can be used for multiple purposes as described herein and as recognized by one of skill in the art.

EXAMPLE 1

Preparation of Magnesium Threonate

Calcium threonate was first prepared from 264 g (1.5 mole) of vitamin C, 300 g (3 moles) of calcium carbonate, and 600 mL of 30% by volume H.sub.2O.sub.2, according to the procedure described by Wei et al., J. Org. Chem. 50, 3462-3467 (1985). The prepared calcium threonate was redissolved in .about.3 L water at .about.90.degree. C. The resulting solution was cooled to .about.50.degree. C. and then poured through a 3 inch-diameter column packed with 3 L clean Amberlite IR-120 strongly acidic resin, while the column was continuously eluted with water. Fractions containing threonic acid having a pH of less than about 4.5 were collected. The fractions of threonic acid were combined (.about.? to .about.8 L) and stirred at .about.50 to .about.60.degree. C. Mg(OH).sub.2 powder was added to the threonic acid in small portions until the pH reached 7. The resulting solution was filtered and concentrated by rotary evaporation at .about.50.degree. C. to a final volume of .about.700 to .about.800 mL. The concentrated solution was cooled to room temperature, filtered to remove any trace amounts of insoluble materials, and then transferred to a 5-L, three-necked, round-bottom flask and mechanically stirred. About 4 L of methanol was added to the resulting solution to precipitate out a white solid product, magnesium threonate. The solid was collected by suction filtration and then dried under high vacuum at 50.degree. C. for 2 days to yield 194 g of magnesium threonate as a white solid. Elemental analysis showed the material contained one mole of water for each mole of magnesium threonate.

EXAMPLE 2

Measurements of Learning Memory Capacity

A group of 10 mice that were genetically altered to present symptoms of Alzheimer's disease (AD) were fed an Mg Diet, a diet of normal solid food and a solution of magnesium threonate and water, for 30 days. The concentration of magnesium threonate in the solution was such that the consumption of a normal amount of the solution corresponded to a total intake of elemental magnesium associated with the magnesium threonate of about 3 mg/day/mouse. Another group, the control group, of 10 mice that were genetically altered to present symptoms of AD were fed a Control Diet, a diet of normal solid food and water, for 30 days.

On the final day of the 30 days of dieting, as described above, each group of mice was trained and tested according to a modified Morris water maze test (Morris et al., Nature 297, 681-683 (1982)), as now described. The pool used was a pool of water in a circular metal tank (150 cm in diameter and 50 cm in depth) having a water height of 30 cm and a water temperature that was maintained at .about.22.degree. C. The pool was placed in a moderately lit area and surrounded by a black curtain. An acrylic platform (15 cm in diameter) was placed 2 cm below the surface of the water in the middle of one quadrant of the pool, equidistant from the center and the edge of the pool. Outside the pool, a cue was placed so as to be visible to a mouse in the maze, allowing a mouse to use it as a landmark for spatial orientation. The cue remained unchanged throughout the test period.

On the first day of the training and testing period, the water in the pool was transparent, such that the platform was visible. Each mouse was trained to swim towards the platform and to stand on the platform so as not to be submerged in the pool. Each mouse underwent a trial, followed by an interval of 1 hour, followed by another trial, and so on, for a total of 5 trials. In each trial, the subject mouse was placed by hand into the pool of water at a starting or release position that was randomly selected from three possible starting positions. The mouse needed to find the platform so as not to be submerged in the pool. If the mouse found the platform, it was allowed to remain there for 30 seconds before it was returned to its home cage. The amount of time the mouse took to find the platform, referred to as "escape latency," was recorded for each trial.

On the second day of the training and testing period, a small quantity of milk was added to the water in the pool, such that the pool was opaque and the platform was no longer visible. Each mouse underwent a trial, followed by an interval of 1 hour, followed by another trial, and so on, for a total of 5 trials. Each trial was as described for the first day of the training and testing period. Once again, each subject mouse placed in the pool needed to find the platform so as not to be submerged in the pool. The amount of time the mouse took to find the platform, or escape latency, was recorded and taken as a measure of the mouse's short-term spatial memory and learning capacity. A lower escape latency measurement was associated with a better learning and memory capacity. If the mouse was unable to find the platform within 90 seconds, it was guided to and placed on the platform for 30 seconds, whereupon the trial was ended and the mouse was given a maximum escape latency score of 90 seconds for the trial.

The two groups of mice underwent further days of training and testing in the manner described above for the second day of the training and testing period. An average escape latency associated with the five trials was calculated for each group of mice for each of days 2-6 of the training and testing period. As the days in training and testing increased, the average escape latency decreased for each group of mice. On and after the third day of the training and testing period, the mice in the magnesium-fortified diet group outperformed the mice in the control group.

EXAMPLE 3

Ameliorative Effects of Magnesium Supplementation on Depression

In this example, a forced swimming test (FST) was used to evaluate anti-depression effects of Magnesium compound. FST is the most widely used tool for assessing antidepressant activity preclinically. The test follows the method described by Porsolt et al., Nature, 266: 730-2 (1977) with a little modification to increase its sensitivity (Cryan et al., Trends Pharmacol. Sci., 23:23845 (2002)). Animals were individually placed into glass cylinders (50 cm height; 20 cm diameter) containing 40 cm of water at 22.degree. C. After 15 min, they were transferred to a 30.degree. C. drying environment for 30 min (the pre-test phase). The animals were returned to the cylinder 24 h later for 5 min (the test phase), and this session was recorded with a video camera. Fresh water was used for each rat and the cylinder was cleaned. Experiments were performed between 10:00 a.m. and 3:00 p.m. Observation of the videotapes was performed by an experimenter unaware of the treatment received by the animals and immobility time measured. A rat was considered immobile when floating and making only the necessary movements to keep its nostrils above the water surface. Additionally, animals behavior during test phase was divided into swimming, climbing and immobility during 5 sec intervals, then data were analyzed as described (Cryan et al., 2002).

A significant reduction in immobility of animals treated with magnesium threonate in comparison with controls was observed after chronic magnesium threonate consumption. Interestingly, the immobility time of magnesium threonate-treated animals significantly correlated with magnesium threonate intake. These results show that, like the effect on cognitive function, magnesium has antidepressant effect also in a dose-pendent fashion. The result suggests that the optimal dosage range and regimen for a magnesium threonate to enhance cognitive function are equally applicable to utilization of magnesium threonate as an antidepressant.

EXAMPLE 4

Increased Lifespan of *Drosophila* Receiving Magnesium Threonate

To examine the effect of magnesium threonate on an animal's lifespan, two standard laboratory inbred strains of *Drosophila*, 2 U and Canton S(CS) wild-type flies, were fed magnesium threonate (MgT). The flies were reared in bottles or vials maintained at 25.degree. C. and 65% humidity on a 12-hour light/12-hour dark cycle. The 2 U line was reared in Cold Spring Harbor's standard laboratory fly medium. The CS line was reared in standard density culture on standard laboratory fly medium. The Magnesium threonate-supplemented media were prepared by adding MgT to vigorously stirred normal molten media at 70.degree. C. The final concentration of MgT in food for the 2 U line was 80, 160, 240 and 400 ug/g, respectively, while the final concentration of compound in food for the CS line was 100, 200, 300 and 500 ug/g, respectively. The flies were initially reared in 30 mL-sized transparent plastic bottles containing 4 mL food media. Newborn flies on the day of eclosion were transferred to medium containing different concentration of MgT for 2 days for mating. After that, male and female flies were transferred to vials (20/vial) under light CO2 anesthesia. There were around 200 flies in each treatment. Flies were transferred to vials containing fresh medium every 2 days and deaths were scored daily.

The results suggest that the benefit of magnesium threonate supplementation is not limited to cognitive function—it improves the overall health of the animal. It also suggests that there exists an optimal magnesium dosage range. Too high a dosage or a body magnesium level can diminish the benefit or even cause harm. Thus, this data also provides further support for establishing the optimal range of supplementation that yields health benefits.

EXAMPLE 5

Effects of Magnesium Supplementation in Cancer Patients Undergoing Chemotherapy

To examine the effects of magnesium threonate on a human that is suffering from one or more types of cancers, and to examine the effects of magnesium threonate on supporting cancer treatment, human subjects as described herein are administered the subject pharmaceutical composition, wherein the composition comprises magnesium threonate.

For example, each human subject is diagnosed with one or more types of cancer such as bladder cancer, using one or more cancer diagnostic methods such as blood tests, imaging, tumor biopsy, and the like. The subjects are then underwent chemotherapy for treating the one or more types of cancers for a period of at least 1 month. In particular, Subject A (a male of 79 years old) diagnosed with bladder cancer was undergoing chemotherapy for about three years. While undergoing chemotherapy, Subject A experienced conditions that can result in a decline of mental state such as depression, anxiety, insomnia, mood swing, fatigue, memory function decline, and the like. Subject A could only sleep 3 or 4 hours every night while undergoing chemotherapy. Upon oral administration of an amount of magnesium threonate, such as 1 g of magnesium threonate for two times a day, or about 2 g of magnesium threonate per day, or in a dosage delivering about 0.15 g of elemental magnesium, for a period of 2, 3 weeks, one month or longer, Subject A exhibited significant improvement in mental capability. For example, Subject A showed reduction of anxiety, ability to sleep through the night, amelioration of depression, reduction of fatigue and/or other conditions that can result in improving the mental states. Also, Subject A showed improvement in memory function, and was able to sleep through the night for 6 hours or more after more than 3 weeks of the magnesium threonate administration. Magnesium threonate supplementation successfully supported the chemotherapy in cancer patients.

EXAMPLE 6

Effects of Magnesium Supplementation in Cancer Patient undergoing surgery

To examine the effects of magnesium threonate on a human that is suffering from one or more types of cancers, and to examine the effects of magnesium threonate on supporting cancer treatment, human subjects as described herein are administered with or without the subject pharmaceutical composition, wherein the composition comprises magnesium threonate.

Human subjects are diagnosed to be suffering from one or more types of cancer (such as brain cancer) using one or more cancer diagnostic methods such as blood tests, imaging, tumor biopsy, and the like. The subjects subsequently undergo surgery to remove the tumor for treating the one or more types of cancers. These human subject consequently experienced conditions that can result in a decline of mental state such as depression, anxiety, insomnia, mood swing, fatigue, and the like during the treatment.

For the treatment of magnesium threonate, in addition to the surgery, these human subjects are orally administered with or without an amount of magnesium threonate, such as 1 g of magnesium threonate for two times a day, or about 2 g of magnesium threonate administered per day, resulting in an elemental magnesium dose of about 0.15 g. The treatment is administered continuously, for example, for more than 2, 3 weeks or one month. The mental state of these human subjects is evaluated.

The test human subjects administered with the subject composition containing magnesium threonate experience significant improvement in mental state after the administration of magnesium threonate. Such improvement is evident by a reduction of anxiety, ability to sleep through the night, and amelioration of depression as compared to the control without being administered Magnesium threonate. These subjects also experience less fatigue and other conditions. Magnesium threonate administration may be able to support the cancer treatment such as surgery in human.

EXAMPLE 7

Effects of Magnesium Supplementation in Cancer Patient Undergoing Radiation Therapy To examine the effects of magnesium threonate on a human that is suffering from one or more types of cancers, and to examine the effects of magnesium threonate on supporting cancer treatment, human subjects as described herein are administered with or without the subject pharmaceutical composition, wherein the composition comprises magnesium threonate.

Human subjects are diagnosed to be suffering from one or more types of cancer (such as brain cancer) using one or more cancer diagnostic methods such as blood tests, imaging, tumor biopsy, and the like. The subjects subsequently undergo radiation therapy to shrink the tumor for treating the one or more types of cancers. These human subject consequently experienced conditions that can result in a decline of mental state such as depression, anxiety, insomnia, mood swing, fatigue, and the like during the treatment.

For the treatment of magnesium threonate, in addition to the surgery, these human subjects are orally administered with or without an amount of magnesium threonate, such as 1 g of magnesium threonate for two times a day, or about 2 g of magnesium threonate administered per day, resulting in an elemental magnesium dose of about 0.15 g. The treatment is administered continuously, for example, for more than 2, 3 weeks or one month. The mental state of these human subjects is evaluated.

The test human subjects administered with the subject composition containing magnesium threonate experience significant improvement in mental state after the administration of magnesium threonate. Such improvement is evident by a reduction of anxiety, ability to sleep through the night, and amelioration of depression as compared to the control without being administered Magnesium threonate. These subjects also experience less fatigue and other conditions. Magnesium threonate administration may be able to support the cancer treatment such as radiation in human.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of treating a solid or cystic tumor in a subject in need thereof, the method comprising:
   administering to the subject in need thereof a pharmaceutical composition comprising an effective amount of magnesium threonate, thereby treating the solid or cystic tumor in the subject in need thereof, wherein the solid or cystic tumor is a cancer selected from the group consisting of: breast cancer, lung cancer, prostate cancer, gastric cancer, head & neck cancer, melanoma, bladder cancer, neuroendocrine cancer, squamous carcinoma, cervical cancer, vulvar cancer, thyroid cancer, pancreatic cancer, renal cancer, esophageal cancer, rectal cancer, penile cancer, multiple myeloma, Merkel cell tumors, ovarian cancer and colorectal cancer.

2. The method of claim 1, further comprising treating the subject with a cancer therapeutic.

3. The method of claim 1, wherein the pharmaceutical composition further comprises one or more anti-cancer agents.

4. The method of claim 1, wherein the subject suffering from the solid or cystic tumor also suffers from depression, anxiety, dementia, insomnia, cognitive impairment, memory function decline, learning capacity decline, migraine, mood swing, hypertension, attention deficit hyperactivity disorder, Alzheimer's disease or Parkinson's disease.

5. The method of claim 1, wherein said administering of the pharmaceutical composition is effective in improving mental state of said subject.

6. The method of claim 1, wherein the pharmaceutical composition is administered orally.

7. The method of claim 1, wherein the effective amount of magnesium threonate administered is in an amount of about 1.5 mg/kg of body weight/day to about 18 mg/kg of body weight/day.

8. The method of claim 1, wherein the pharmaceutical composition is administered for at least about 1 month.

9. The method of claim 1, wherein the pharmaceutical composition is administered for at least about 1 week.

10. The method of claim 1, wherein said effective amount is an amount capable of achieving a physiological concentration of magnesium at 0.75 mM or above in serum, plasma, or cerebrospinal fluid.

11. The method of claim 1, wherein said effective amount is an amount capable of increasing a physiological concentration of magnesium by at least 10% as compared to an initial level of magnesium prior to administration of it to said subject.

12. The method of claim 1, wherein the pharmaceutical composition is contained in a foodstuff.

13. The method of claim 1, wherein the effective amount of magnesium threonate is in an amount of less than 1.5 mg/kg of body weight/day.

14. The method of claim 1, wherein the effective amount of magnesium threonate is in an amount of about 9 mg/kg of body weight/day to 18 mg/kg of body weight/day.

15. The method of claim 1, wherein the effective amount of magnesium threonate is in an amount of more than 18 mg/kg of body weight/day.

* * * * *